(12) United States Patent
Dijkstra

(10) Patent No.: US 11,547,869 B2
(45) Date of Patent: Jan. 10, 2023

(54) SHAPE COMPLIANT WEARABLE PHOTO-DYNAMIC THERAPY (PDT) PAD

(71) Applicant: Light Tree Ventures Holding B.V., The Hague (NL)

(72) Inventor: Alain Dijkstra, Amstelveen (NL)

(*) Notice: Subject to any disclaimer, the term of this patent is extended or adjusted under 35 U.S.C. 154(b) by 0 days.

(21) Appl. No.: 17/231,035

(22) Filed: Apr. 15, 2021

(65) Prior Publication Data

US 2022/0331605 A1    Oct. 20, 2022

(51) Int. Cl.
*A61N 5/06* (2006.01)
*A61M 35/00* (2006.01)

(52) U.S. Cl.
CPC .............. *A61N 5/06* (2013.01); *A61M 35/30* (2019.05); *A61N 2005/0632* (2013.01); *A61N 2005/0652* (2013.01)

(58) Field of Classification Search
CPC .............. A61N 5/06; A61N 2005/0632; A61N 2005/0652; A61M 35/30
See application file for complete search history.

(56) References Cited

U.S. PATENT DOCUMENTS

| | | |
|---|---|---|
| 5,358,503 A | 10/1994 | Bertwell et al. |
| 6,290,713 B1 * | 9/2001 | Russell ................ A61N 5/0616 607/91 |
| 7,147,653 B2 | 12/2006 | Williams et al. |
| 9,901,745 B2 | 2/2018 | Bembridge et al. |
| 2011/0190749 A1 * | 8/2011 | McMillan ................ A61N 5/06 606/16 |
| 2013/0274839 A1 * | 10/2013 | Johnson ............... A61N 5/0616 607/90 |
| 2014/0128942 A1 * | 5/2014 | Bembridge .......... A61N 5/0613 607/90 |
| 2014/0288351 A1 * | 9/2014 | Jones .................... A61N 5/0624 607/90 |
| 2016/0045757 A1 * | 2/2016 | Groseth ............. A61K 41/0061 604/20 |
| 2021/0154093 A1 * | 5/2021 | Boone, III ......... A61H 23/0263 |

FOREIGN PATENT DOCUMENTS

WO    WO-2018046967 A1 *   3/2018    ............. A61B 18/18

* cited by examiner

*Primary Examiner* — Gary Jackson
*Assistant Examiner* — Sebastian X Lukjan
(74) *Attorney, Agent, or Firm* — Willie Jacques; Emanus, LLC

(57) ABSTRACT

A shape compliant wearable Photo-Dynamic Therapy (PDT) pad comprises an outer layer having an outer surface adapted to be exposed to the ambient, an inner layer having an inner surface adapted to be in contact with a body of a user, a metallic sheet provided between the outer layer and the inner layer, the metallic sheet being shape compliant, and a plurality of Light Emitting Diodes (LEDs) provided between the inner layer and the outer layer. The plurality of LEDs is configured to emit electromagnetic radiation towards the body of the user. Also, the inner layer and the metallic sheet include an enclosed cavity therebetween, the metallic sheet is configured to be maintained at a negative potential, and the inner layer includes a plurality of air holes providing a passage for ambient air to enter and exit the enclosed cavity.

8 Claims, 4 Drawing Sheets

SHAPE COMPLIANT WEARABLE PHOTO-DYNAMIC THERAPY (PDT) PAD

TECHNICAL FIELD

The present invention relates generally to devices used to deliver Photo-Dynamic Therapy (PDT). More specifically, the present invention relates to wearable pads that are used to deliver the PDT to several parts of the human body.

BACKGROUND ART

Wearable pads made out of fabric or flexible polymeric materials for delivering Photo-Dynamic Therapy (PDT) to several parts of the human body, such as the spine, the arms, the thighs, and the knees, etc. have been in the market for quite some time. Such wearable pads include arrays of several spatially arranged and distinct Light Emitting Diodes (LEDs) that generally emit electromagnetic radiations in red and/or infrared frequencies of the electromagnetic spectrum. The more recent designs of the wearable pads have come to include built-in rechargeable batteries that may be charged through a power cable.

However, such wearable pads are very rudimentary in construction, and generally serve only a single purpose of delivering electromagnetic radiation to the human body. Moreover, with the LEDs being spaced apart spatially, in the forms of two-dimensional arrays, the wearable pads fail to effectively utilize the entire surface area available on a surface that comes in contact with the human body. Also, all such wearable pads require one or the other kind of a fastening arrangement, such as loop and hook fasteners, straps with buckles, or button and holes, to keep them in a desired portion of the human body, without getting displaced. As a result, as the fastening arrangement wears off or becomes dysfunctional, the entire wearable pad needs to be discarded as those wearable pads are not generally designed for repair in the first place.

Therefore, there is a need in the art for a shape compliant wearable PDT pad, which does not suffer from the aforementioned deficiencies.

OBJECTS OF THE INVENTION

Some of the objects of the present invention are as follows:

It is an object of the invention to provide a wearable pad for light therapy, which is shape compliant and can be worn at any part of the body.

It is another object of the invention, that the wearable pad should also be capable of providing negative ion therapy.

It is yet another object of the invention that the wearable pad be made up light weight material and be portable.

SUMMARY

The present invention is described hereinafter by various embodiments. This invention may, however, be embodied in many different forms and should not be construed as limited to the embodiment set forth herein. Rather, the embodiment is provided so that this disclosure will be thorough and complete and will fully convey the scope of the invention to those skilled in the art.

According to an aspect of the present invention, there is provided a shape compliant wearable Photo-Dynamic Therapy (PDT) pad, the wearable PDT pad comprising an outer layer having an outer surface adapted to be exposed to the ambient, an inner layer having an inner surface adapted to be in contact with a body of a user, a metallic sheet provided between the outer layer and the inner layer, the metallic sheet being shape compliant, and a plurality of Light Emitting Diodes (LEDs) provided between the inner layer and the outer layer. The plurality of LEDs is configured to emit electromagnetic radiation towards the body of the user. The inner layer and the metallic sheet include an enclosed cavity therebetween. Further, the metallic sheet is configured to be maintained at a negative potential, and the inner layer includes a plurality of air holes providing a passage for ambient air to enter and exit the enclosed cavity.

In one embodiment of the present invention, the shape compliant wearable PDT pad further comprises a plurality of support baffles provided between the inner layer and the metallic sheet. The plurality of support baffles has been provided within the enclosed cavity.

In one embodiment of the invention, the outer layer is made up of an opaque silicone material and the inner layer is made up of a diaphanous silicone material.

In one embodiment of the invention, the inner surface of the inner layer has been provided with an anti-microbial coating.

In one embodiment of the invention, the metallic sheet includes a plurality of conical holes to accommodate the plurality of respective LEDs, the plurality of conical holes being provided with a reflective coating.

In one embodiment of the invention, the metallic sheet is made up of a ferromagnetic material.

In another embodiment of the invention, one or more of the inner layer and the outer layer includes a plurality of air holes in respective central regions and along the edges of the one or more of the inner layer and the outer layer.

In yet another embodiment of the present invention, the plurality of conical holes is co-axial with the plurality of air holes.

In the context of the specification, the term "diaphanous materials" refers to the materials that allow the transmission of electromagnetic radiation, including at least Ultra-Violet (UV), visible light, and Infrared (IR), through them.

In the context of the specification, the term "refractive index" of a material refers to the ratio of the speed of electromagnetic radiation (such as light) in a medium formed from such material to the speed of radiation in a pure vacuum.

In the context of the specification, terms like "light", "radiation", "irradiation", "emission" and "illumination", etc. have been used synonymously and refer to electromagnetic radiation in a frequency range varying from the Ultra-violet (UV) frequencies to Infrared (IR) frequencies and wavelengths, wherein the frequency range is inclusive of UV and IR frequencies and wavelengths. It is to be further noted here that UV radiation can be categorized in several manners depending on respective wavelength ranges, all of which are envisaged to be under the scope of this invention. For example, UV radiation can be categorized as, Hydrogen Lyman-α (122-121 nm), Far UV (200-122 nm), Middle UV (300-200 nm), Near UV (400-300 nm). The UV radiation may also be categorized as UVA (400-315 nm), UVB (315-280 nm), and UVC (280-100 nm). Similarly, IR radiation may also be categorized into several categories according to respective wavelength ranges which are again envisaged to be within the scope of this invention. A commonly used subdivision scheme for IR radiation includes Near IR (0.75-1.4 µm), Short-Wavelength IR (1.4-3 µm), Mid-Wavelength IR (3-8 µm), Long-Wavelength IR (8-15 µm), and Far IR (15-1000 µm).

In the context of the specification, the term "silicone" represents polymers made up of siloxane (—R2Si—O—SiR2—, where R=organic group).

The following detailed description is illustrative and is not intended to be in any way limiting. In addition to the illustrative aspects, embodiments, and features described above, further aspects, embodiments, and features will be apparent by reference to the following detailed description in conjunction with the accompanying drawings.

BRIEF DESCRIPTION OF DRAWINGS

So that the manner in which the above-recited features of the present invention can be understood in detail, a more particular description of the invention, briefly summarized above, may have been referred by examples, some of which are illustrated in the appended drawings. It is to be noted, however, that the appended drawings illustrate only typical examples of this invention and are therefore not to be considered limiting of its scope, for the invention may admit to other equally effective examples.

These and other features, benefits, and advantages of the present invention will become apparent by reference to the following text figure, with like reference numbers referring to like structures across the views, wherein.

DETAILED DESCRIPTION

Figure 1:
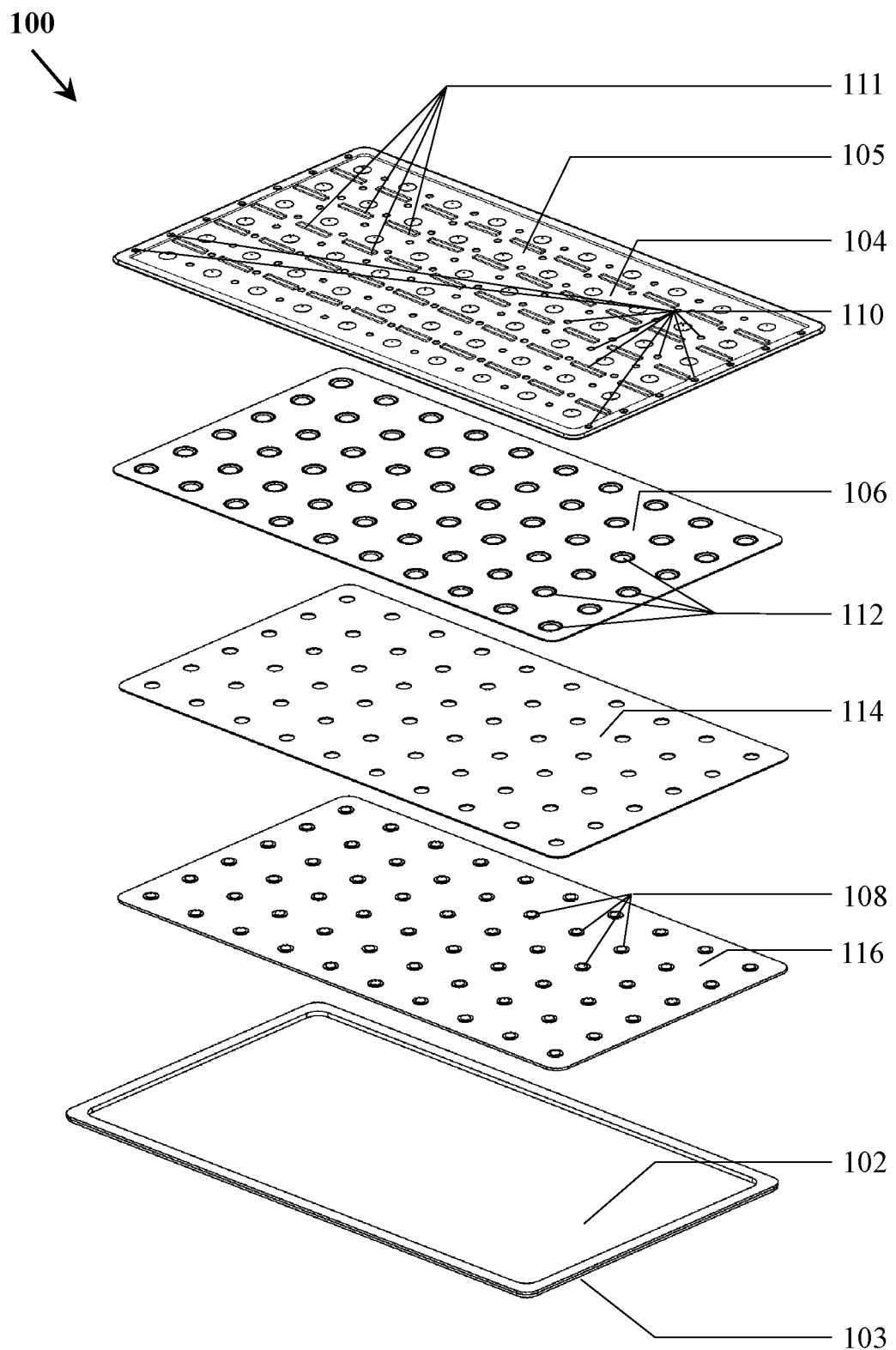
FIG. 1 illustrates an exploded view of a shape compliant wearable Photo-Dynamic Therapy (PDT) pad, in accordance with an embodiment of the present invention.

While the present invention is described herein by way of example using embodiments and illustrative drawings, those skilled in the art will recognize that the invention is not limited to the embodiments of drawing or drawings described, and are not intended to represent the scale of the various components. Further, some components that may form a part of the invention may not be illustrated in certain figures, for ease of illustration, and such omissions do not limit the embodiments outlined in any way. It should be understood that the drawings and detailed description thereto are not intended to limit the invention to the particular form disclosed, but on the contrary, the invention is to cover all modifications, equivalents, and alternatives falling within the scope of the present invention as defined by the appended claim. As used throughout this description, the word "may" is used in a permissive sense (i.e. meaning having the potential to), rather than the mandatory sense, (i.e. meaning must). Further, the words "a" or "an" mean "at least one" and the word "plurality" means "one or more" unless otherwise mentioned. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes. Any discussion of documents, acts, materials, devices, articles, and the like is included in the specification solely for the purpose of providing a context for the present invention. It is not suggested or represented that any or all of these matters form part of the prior art base or were common general knowledge in the field relevant to the present invention.

In this disclosure, whenever a composition or an element or a group of elements is preceded with the transitional phrase "comprising", it is understood that we also contemplate the same composition, element, or group of elements with transitional phrases "consisting of, "consisting", "selected from the group of consisting of, "including", or "is" preceding the recitation of the composition, element or group of elements and vice versa. The present invention is described hereinafter by various embodiments with reference to the accompanying drawing, wherein reference numerals used in the accompanying drawing correspond to the like elements throughout the description. This invention may, however, be embodied in many different forms and should not be construed as limited to the embodiment set forth herein. Rather, the embodiment is provided so that this disclosure will be thorough and complete and will fully convey the scope of the invention to those skilled in the art. In the following detailed description, numeric values and ranges are provided for various aspects of the implementations described. These values and ranges are to be treated as examples only and are not intended to limit the scope of the claims. Also, several materials are identified as suitable for various facets of the implementations. These materials are to be treated as exemplary and are not intended to limit the scope of the invention.

It is envisaged that a wearable Photo-Dynamic Therapy (PDT) pad (hereinafter referred to as "the wearable pad" be provided that is supposed to be foldable to any desired shape and can take the shape of any part of the human body that it is worn on. Since the wearable pad is envisaged to be used several times, the shape compliance is envisaged to be achieved through providing a metallic sheet in between an inner and outer layer of the wearable pad. The rationale behind using the metallic sheet is that metals generally have high moduli of elasticity and therefore can survive several cycles of bending and unbending (or straightening). Also, the metals are good conductors of electricity and the metallic sheet can be used as a negatively charged electrode for providing negative ion therapy to a user. Several Light Emitting Diodes (LEDs) have been provided between the inner and the outer layer to provide the intended PDT. The LEDs may be operable for a range of frequencies of the electromagnetic spectrum, varying between Infrared (IR) and Ultraviolet (UV) frequencies, the range inclusive of all IR and UV frequencies. Also, reflective cones have been provided around LEDs to direct electromagnetic radiation, which would otherwise have been dissipated to the ambient, towards the body of the user. The inner layer that is supposed to be in contact with the body of the user has also been provided with anti-microbial coatings to further enhance the therapeutic benefits of the wearable pad. Referring to the figures, the invention will be described in further detail.

FIG. 1 illustrates an exploded view of a shape compliant wearable Photo-Dynamic Therapy (PDT) pad 100, in accordance with an embodiment of the present invention. As illustrates in FIG. 1, the shape compliant wearable Photo-Dynamic Therapy (PDT) pad 100 (hereinafter referred to as "the wearable pad 100") includes an outer layer 102 having an outer surface 103 adapted to be exposed to the ambient. In several embodiments, the outer layer 102 is envisaged to be opaque to prevent loss of electromagnetic radiations emitted by the LEDs from escaping towards the ambient. The wearable pad 100 further includes an inner layer 104 having an inner surface 105 adapted to be in contact with the body of a user. In that regard, the inner layer 104 is envisaged to be made up of diaphanous material. However, both the inner layer 104 and the outer layer 102 are envisaged to be made up of flexible, inert, and skin-friendly materials that do not cause any negative effects on the skin of the user. Such materials may include silicones such as Poly Di-Methyl-Siloxane (PDMS). In several embodiments, the inner surface 105 may also be provided with anti-microbial coatings such as ZnO and $TiO_2$ that inhibit the growth of pathogens such as bacteria, fungi, viruses. These metal oxides can also release reactive oxygen species (ROS) to kill bacteria under UV irradiation.

Further, the wearable pad 100 includes a metallic sheet 106 provided between the outer layer 102 and the inner layer 104. The metallic sheet 106 is envisaged to shape compliant. In that regard, the thickness of the metallic sheet 106 may vary between 0.5 mm (0.02 inches) to 6 mm (0.25 inches). It is further envisaged that the metallic sheet 106 be made of a ferromagnetic material, such as, but not limited to, iron, cobalt, nickel, and their alloys. The ferromagnetism of the metallic sheet 106 would allow locking of the wearable pad 100 through magnetic fasteners once the wearable pad 100 has been worn on the desired part of the body of the user. Such magnetic fasteners may be easily located and removed from the wearable pad 100, owing to the ferromagnetism of the metallic sheet 106. The metallic sheet 106 is configured to be maintained at a negative potential for the generation of negative ions. The maintenance of the negative potential at the metallic sheet 106, using a Direct Current (DC) power source, such as a battery, can be understood from United States Patent Numbered U.S. Pat. No. 6,703,785B2, titled "Negative Ion Generator", and assigned to Andes Electric Co. Ltd.

The wearable pad 100 further includes a plurality of LEDs 108 installed on a Printed Circuit Board (PCB) 116. The plurality of LEDs 108 is configured to emit electromagnetic radiation towards the body of the user, and therefore, are directed towards the inner surface 105. The LEDs, in general, are characterized by their superior power efficiencies, smaller sizes, rapidity in switching, physical robustness, and longevity when compared with incandescent or fluorescent lamps. In that regard, the plurality of LEDs 108 may be through-hole type LEDs (generally used to produce electromagnetic radiations of red, green, yellow, blue, and white colors), Surface Mount LEDs, Bi-color LEDs, Pulse Width Modulated RGB (Red-Green-Blue) LEDs, and high power LEDs, etc. In that regard, the PCB 116 is also envisaged to shape compliant and/or at least partially flexible. There is also provided an insulation layer 114 between the metallic sheet 106 and the PCB 116 to prevent the metallic sheet 106 from shorting the PCB 116. The insulation layer 114 may be made up of an electrically insulating and flexible polymer.

In several alternate embodiments, the plurality of LEDs 108 may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on the generation of OLED panels can be found in Bardsley, J.N. (2004), "International OLED Technology Roadmap", IEEE Journal of Selected Topics in Quantum Electronics, Vol. 10, No. 1, that is included herein in its entirety, by reference. An exemplary description of flexible inorganic light-emitting diode strips can be found in granted United States Patent Numbered U.S. Pat. No. 7,476,557B2, titled "Roll-to-roll fabricated light sheet and encapsulated semiconductor circuit devices", which is included herein in its entirety, by reference. In several embodiments, the plurality of LEDs 108 may also be micro-LEDs described through US Patent Numbers U.S. Pat. No. 8,809,126B2, U.S. Pat. No. 8,846,457B2, U.S. Pat. No. 8,852,467B2, U.S. Pat. No. 8,415,879B2, U.S. Pat. No. 8,877,101B2, U.S. Pat. No. 9,018,833B2, and their respective family members, assigned to NthDegree Technologies Worldwide Inc, which are included herein by reference, in their entirety. The plurality of LEDs 108, in that regard, may be provided as a printable composition of the micro-LEDs, printed on a substrate.

A person skilled in the art would appreciate that white and other colored lightings may be produced using phosphor coatings such as Yttrium Aluminum Garnet (YAG) in combination with a blue LED to generate white light and Magnesium doped potassium fluorosilicate in combination with blue LED to generate red light. Additionally, near Ultra Violet (UV) LEDs may be combined with Europium based phosphors to generate red and blue lights and Copper and Zinc doped Zinc Sulfide based phosphors to generate green light. Therefore, the inner layer 104 may also be either coated or impregnated with phosphor materials to generate irradiation of varying frequencies as per the application of the wearable pad 100. The inner layer 104 further includes a plurality of air holes 110 and the metallic sheet 106 further includes a plurality of conical holes 112 to accommodate the plurality of respective LEDs 108. The plurality of air holes 110 can be provided both in central region of the wearable pad 100 and along the edges. The plurality of air holes 110 may also equivalently be provided in the outer layer 102. In several embodiments of the invention, the wearable pad 100 also includes a plurality of support baffles 111 between the inner layer 104 and the metallic sheet 106 to prevent the inner layer 104 from collapsing onto, or bending and contacting, the metallic sheet 106 during use.

Figure 2A:
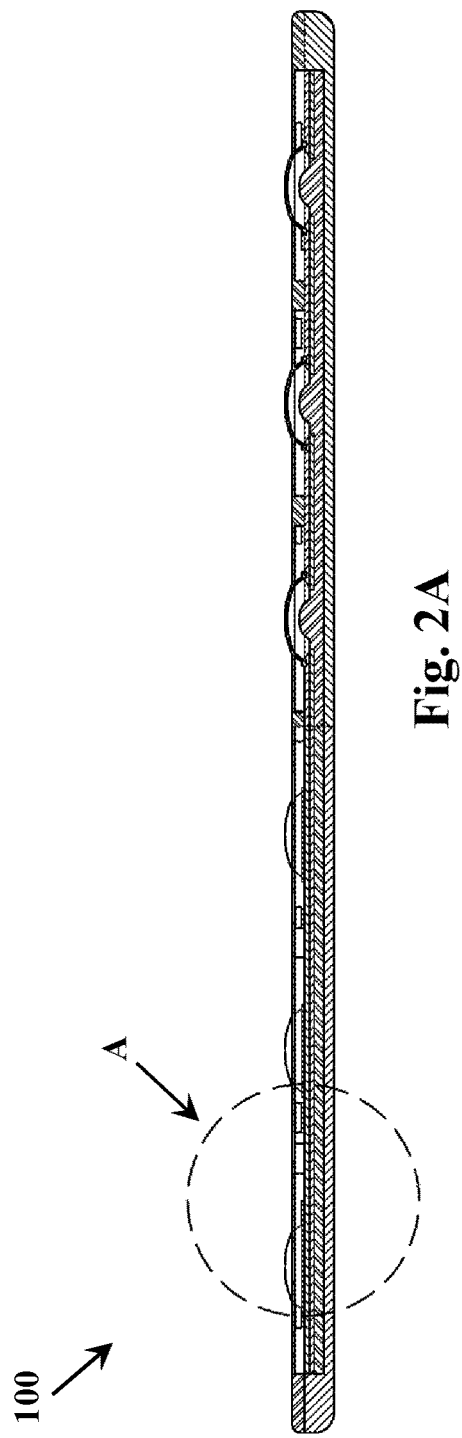
FIG. 2A illustrates a central sectional view of the shape compliant wearable PDT pad of FIG. 1.
Figure 2B:
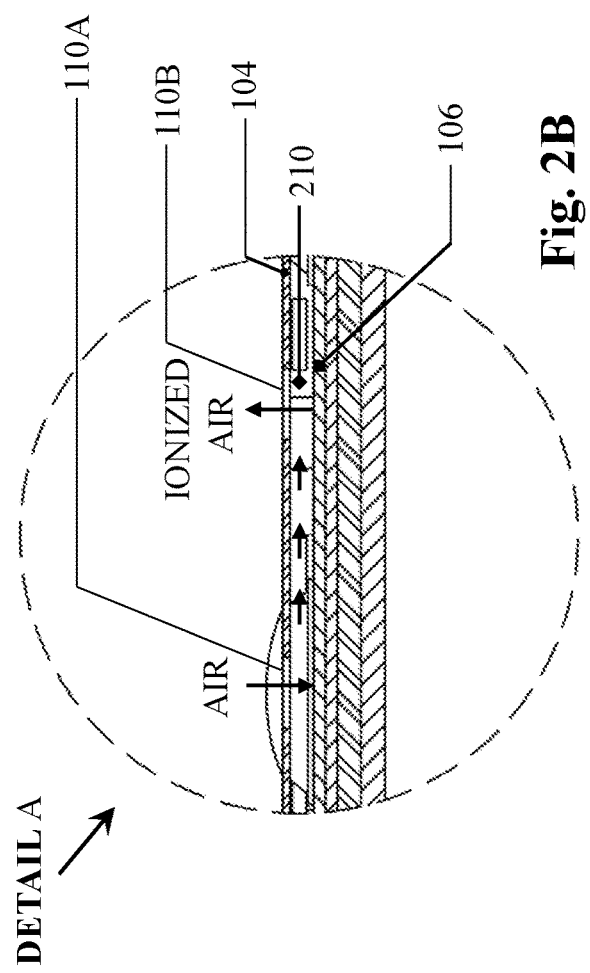
FIG. 2B illustrates an enlarged view of a portion 'A' of the shape compliant wearable PDT pad of FIG. 2A.

FIG. 2A illustrates a central sectional view of the wearable pad 100 of FIG. 1. FIG. 2B illustrates an enlarged view of a portion 'A' of the wearable pad 100 of FIG. 2A. As depicted in FIGS. 2A and 2B, the inner layer 104 and the metallic sheet 106 include an enclosed cavity 210 therebetween. The plurality of air holes 110 of the inner layer 104 provides a passage for ambient air to enter and exit the enclosed cavity 210. For example, as depicted in FIG. 2B, the ambient air may enter into the enclosed cavity 210, through a first air hole 110A of the inner layer 104, and get ionized by coming in contact with the metallic sheet 106 that has been maintained at the negative potential. The ionized air carrying negative ions may then exit the enclosed cavity 210 through a second air hole 110B of the inner layer 104. In that regard, the wearable pad 100 would also be able to provide negative air ionization therapy to the user, in addition to the PDT being provided by the plurality of LEDs 108. The benefits of the negative air ionization therapy on the human body and other laboratory animal subjects can be understood from Jiang, Shu-Ye et al. *"Negative Air Ions and Their Effects on Human Health and Air Quality Improve-* ment." *International Journal of Molecular Sciences* vol. 19, 10 2966. 28 Sep. 2018, DOI: 10.3390/ijms19102966, which is included herein by reference, in its entirety.

Figure 3A:
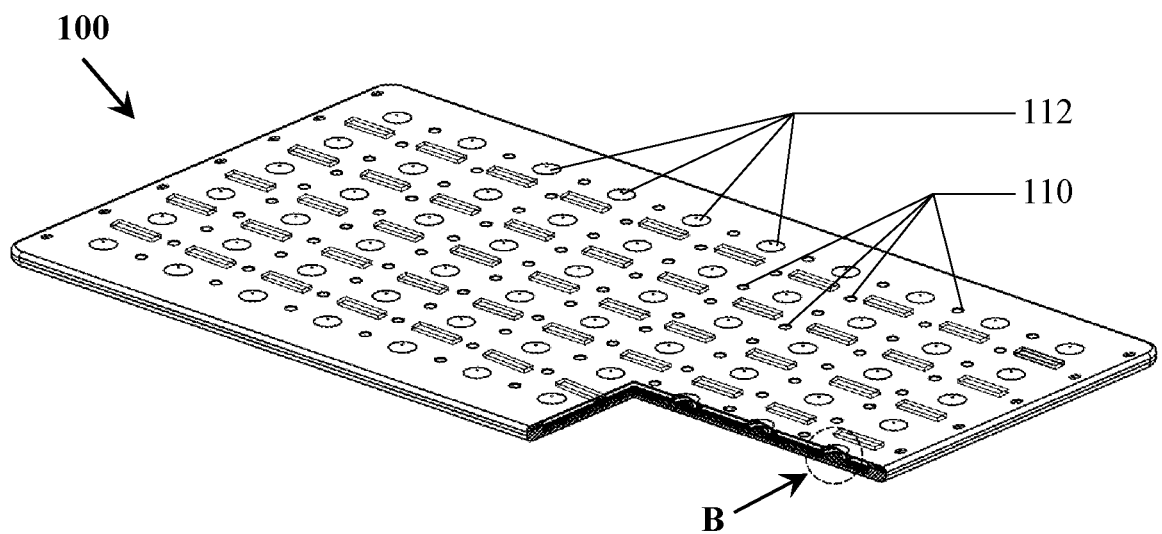
FIG. 3A illustrates a perspective view of the sectioned shape compliant wearable PDT pad of FIG. 1A.
Figure 3B:
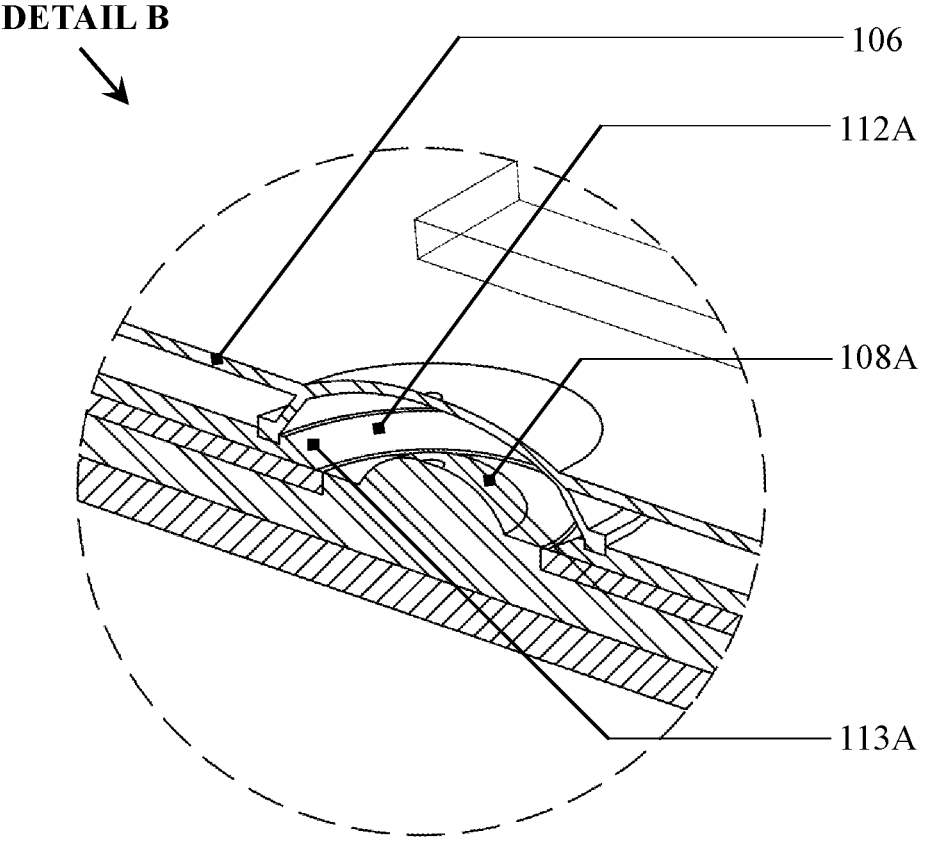
FIG. 3B illustrates an enlarged view of a portion 'B' of the shape compliant wearable PDT pad of FIG. 3A.

FIG. 3A illustrates a perspective view of the partially sectioned wearable pad 100 of FIG. 1A. It can be observed from FIG. 3A that the plurality of air holes 110 and the plurality of conical holes 112 are offset from each other. However, in several alternate embodiments, the plurality of air holes 110 and the plurality of conical holes 112 may also be co-axial with each other, thereby allowing savings in material and production costs. FIG. 3B illustrates an enlarged view of a portion '13' of the wearable pad 100 of FIG. 3A. As depicted in FIGS. 3A and 3B, the metallic sheet 106 includes a conical hole 112A of the plurality of conical holes 112, to accommodate an LED 108A of the plurality of LEDs 108. It is envisaged that a conical surface 113A of the conical hole 112A has been coated with reflective material which is popularly known in the art as Highly Reflective Coating. A Highly Reflective Coating is a thin film or layers of films that are deposited on a substrate to enhance the reflecting property of the substrate. Metallic silver (Ag), gold (Au), and aluminum (Al) are the most widely studied as highly reflective materials. Other materials such as different nano-crystalline metal oxides —TiO2, ZnO, MgO, and Al2O3 are widely used as IR reflectors. MgF2 and AlF3 protected Al films have reflectors in the UV spectral region. More information on Highly Reflective Coatings can be found in Prasad K, Goyal A, Gohil K, Jagyasi I (2018), *"Highly reflective coatings"*. *International Journal of Applied Engineering Research* 13(22), pp.:15773-15782, which is included herein by reference, in its entirety. The presence of Highly Reflective Coatings on the conical surfaces of the plurality of conical holes 112 would redirect to the body of the user, any residual irradiation from the plurality of LEDs 108, which would otherwise have been directed away from the body of the user. This will both increase the overall irradiating area on the inner surface 105 thereby utilizing a much larger surface area of the wearable pad 100 for PDT, but will also reduce glare from the plurality of LEDs 108 by diffusing the residual and misdirected irradiation, while also thereby increasing the therapeutic efficacy of the wearable pad 100.

Figure 4A:
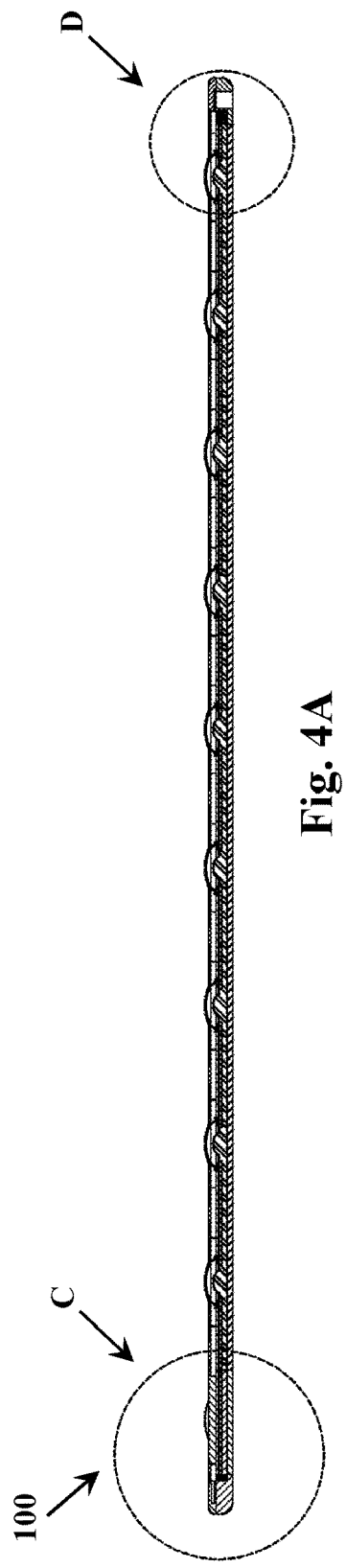
FIG. 4A illustrates a shape compliant wearable Photo-Dynamic Therapy (PDT) pad, in accordance with another embodiment of the present invention.
Figure 4C:
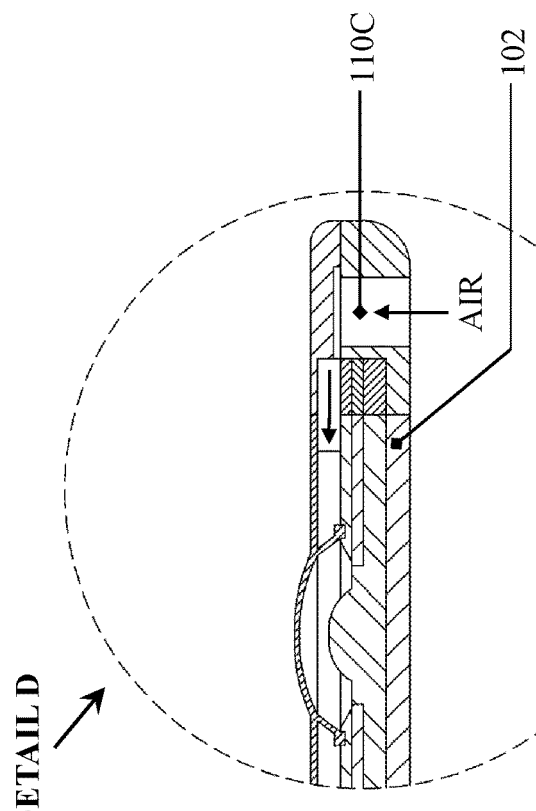
FIG. 4C illustrates an enlarged view of a portion 'D' of the shape compliant wearable PDT pad of FIG. 4A.
Figure 4B:
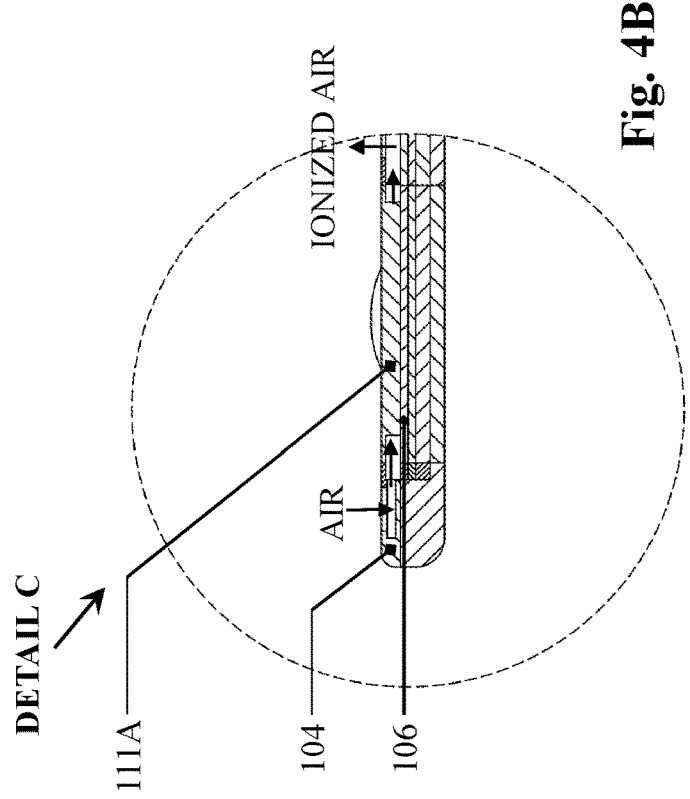
FIG. 4B illustrates an enlarged view of a portion 'C' of the shape compliant wearable PDT pad of FIG. 4A.

FIG. 4A illustrates the wearable pad 100, in accordance with another embodiment of the present invention. FIG. 4B illustrates an enlarged view of a portion 'C' of the wearable pad 100 of FIG. 4A. As illustrated in FIG. 4B, a support baffle 111A of the plurality of support baffles 111 has been provided between the inner layer 104 and the metallic sheet 106 to prevent the inner layer 104 from collapsing onto the metallic sheet 106. FIG. 4C illustrates an enlarged view of a portion 'D' of the wearable pad of 100 FIG. 4A. As depicted in FIG. 4C, an air hole 110C of the plurality of air holes 110 has been provided in the outer layer 102 of the wearable pad 100. The inclusion of at least some of the plurality of air holes 110 in the outer layer 102 allows the ionization therapy to be available to the user even when the inner layer 104 is in contact with their body in an airtight manner.

The wearable pad as described above offers several advantages. First, the wearable pad is pliable because of the presence of the metallic sheet, and owing to sufficiently high moduli of elasticity of metals, the wearable pad can be bent into any desired shape and then straightened several times ensuring the longevity of the overall wearable pad. The ferromagnetism of the metallic sheet would allow the utilization of detachable magnetic fasteners for keeping the wearable pad in its place during usage. Several LED and phosphor coatings can be combined to achieve several distinct wavelengths making the wearable pad adaptable for a wide range of therapeutic applications ranging from skin treatment and treatment of lesions with the help of UV radiation, and up to muscle relaxation with the help IR radiation. The conical surfaces provided around the LEDs would help in redirecting the residual irradiation from the LEDs to the human body, thereby increasing the overall therapeutic efficacy of the wearable pad, while also diffusing the residual irradiation to reduce glare from the wearable pad. Also, the wearable pad is not limited to PDT applications alone, but also provides an added benefit of negative ion therapy, making the wearable pad a cost-effective multipurpose device.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to be providing broadest scope of consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. A shape compliant wearable Photo-Dynamic Therapy (PDT) pad, the wearable PDT pad comprising:
   an outer layer having an outer surface adapted to be exposed to the ambient;
   an inner layer having an inner surface adapted to be in contact with a body of a user;
   a metallic sheet provided between the outer layer and the inner layer, the metallic sheet being shape compliant; and
   a plurality of Light Emitting Diodes (LEDs) provided between the inner layer and the outer layer;
   wherein the plurality of LEDs are configured to emit electromagnetic radiation towards the body of the user; and
   wherein the inner layer and the metallic sheet include an enclosed cavity therebetween, the metallic sheet is configured to be maintained at a negative potential, and the inner layer includes a plurality of air holes providing a passage for ambient air to enter and exit the enclosed cavity.

2. The shape compliant wearable PDT pad as claimed in claim 1, wherein the outer layer is made up of an opaque silicone material and the inner layer is made up of a diaphanous silicone material.

3. The shape compliant wearable PDT pad as claimed in claim 1, wherein the metallic sheet includes a plurality of conical holes to accommodate the plurality of respective LEDs, the plurality of conical holes being provided with a reflective coating.

4. The shape compliant wearable PDT pad as claimed in claim 1, wherein the metallic sheet is made up of a ferromagnetic material.

5. The shape compliant wearable PDT pad as claimed in claim 1, wherein one or more of the inner layer and the outer layer include a plurality of air holes in respective central regions and along the edges of the one or more of the inner layer and the outer layer.

6. The shape compliant wearable PDT pad as claimed in claim 5, wherein the metallic sheet includes a plurality of conical holes to accommodate the plurality of respective LEDs, the plurality of conical holes being co-axial with the plurality of air holes.

7. The shape compliant wearable PDT pad as claimed in claim 5, wherein the metallic sheet includes a plurality of conical holes to accommodate the plurality of respective LEDs, the plurality of conical holes being offset from the plurality of air holes.

8. The shape compliant wearable PDT pad as claimed in claim 1, further comprising a plurality of support baffles between the inner layer and the metallic sheet.

\* \* \* \* \*